US008589177B2

(12) United States Patent
Haq

(10) Patent No.: US 8,589,177 B2
(45) Date of Patent: *Nov. 19, 2013

(54) VIRTUAL CLINIC FOR MEDICAL PRACTICE

(76) Inventor: Mohamed Haq, Friendswood, TX (US)

( * ) Notice: Subject to any disclaimer, the term of this patent is extended or adjusted under 35 U.S.C. 154(b) by 1406 days.

This patent is subject to a terminal disclaimer.

(21) Appl. No.: 12/169,554

(22) Filed: Jul. 8, 2008

(65) Prior Publication Data

US 2008/0275311 A1 Nov. 6, 2008

Related U.S. Application Data

(63) Continuation-in-part of application No. 09/918,413, filed on Jul. 30, 2001, now Pat. No. 7,412,396, and a continuation-in-part of application No. 09/760,917, filed on Jan. 16, 2001, now abandoned.

(60) Provisional application No. 60/269,051, filed on Feb. 15, 2001.

(51) Int. Cl.
*G06Q 50/00* (2012.01)
*G06Q 10/00* (2012.01)

(52) U.S. Cl.
USPC .................................................. 705/2; 705/3

(58) Field of Classification Search
USPC ............................................................ 705/2
See application file for complete search history.

(56) References Cited

U.S. PATENT DOCUMENTS

| | | | | |
|---|---|---|---|---|
| 4,270,174 A | * | 5/1981 | Karlin et al. | 701/115 |
| 5,911,687 A | * | 6/1999 | Sato et al. | 600/300 |
| 6,018,713 A | * | 1/2000 | Coli et al. | 705/2 |
| 6,256,613 B1 | * | 7/2001 | Falchuk et al. | 705/2 |
| 6,403,897 B1 | * | 6/2002 | Bluth et al. | 177/144 |
| 6,704,410 B1 | * | 3/2004 | McFarlane et al. | 379/265.05 |
| 7,412,396 B1 | * | 8/2008 | Haq | 705/2 |
| 2002/0010608 A1 | * | 1/2002 | Faber et al. | 705/8 |
| 2002/0065682 A1 | * | 5/2002 | Goldenberg | 705/2 |

OTHER PUBLICATIONS

Hu, Examining the technology acceptance model using physician acceptance of telemedicine technology, J. Manage. Inf. Syst. 16, 2 (Sep. 1999), 91-112.*

* cited by examiner

*Primary Examiner* — Tran Nguyen
(74) *Attorney, Agent, or Firm* — Sheppard, Mullin, Richter & Hampton LLP

(57) ABSTRACT

A method is provided for a virtual clinic to establish communications between a user (e.g., a patient) and a specialist (e.g., a physician) in order to facilitate a diagnosis. In various embodiments, a user provides a request for the specialist to a virtual clinic. The request may be a request for medical services identifying medical needs. The user may then receive specialist information from the virtual clinic. The virtual clinic may establish real-time communication between the user and a specialist. The user may receive instructions from the specialist via the virtual clinic to perform a test. The user may then report a test result from the test to the specialist via the virtual clinic. The virtual clinic may receive and store a diagnosis from the specialist.

38 Claims, 6 Drawing Sheets ly owned U.S. patent application Ser. No. 09/918,413, filed Jul. 30, 2001 now U.S. Pat. No. 7,412,396, entitled "Virtual Clinic for Medical Practice," which is a conversion of, and claims priority to, commonly owned U.S. Provisional patent application No. 60/269,051, filed Feb. 15, 2001, entitled "Electronic Business Entity for Medical Practice" by Mohamed M. Haq which are both hereby incorporated by reference. This application is also a continuation-in-part of U.S. Nonprovisional patent application Ser. No. 09/760,917, entitled "Computer System for Assisting a Physician," filed Jan. 16, 2001 now abandoned which is hereby incorporated by reference.

VIRTUAL CLINIC FOR MEDICAL PRACTICE

CROSS-REFERENCE TO RELATED APPLICATION

This patent application is a continuation in part of commonly owned U.S. patent application Ser. No. 09/918,413, filed Jul. 30, 2001 now U.S. Pat. No. 7,412,396, entitled "Virtual Clinic for Medical Practice," which is a conversion of, and claims priority to, commonly owned U.S. Provisional patent application No. 60/269,051, filed Feb. 15, 2001, entitled "Electronic Business Entity for Medical Practice" by Mohamed M. Haq which are both hereby incorporated by reference. This application is also a continuation-in-part of U.S. Nonprovisional patent application Ser. No. 09/760,917, entitled "Computer System for Assisting a Physician," filed Jan. 16, 2001 now abandoned which is hereby incorporated by reference.

BACKGROUND

1. Field of the Invention

The present invention relates generally to a system and method for a patient to contact a physician remotely and to receive medical services via a virtual clinic which contracts with doctors and insurance companies, and allows for the patient to submit remotely diagnostic information from his/her home so that a physician may make a diagnosis and recommend treatment.

2. Background of the Related Technology

In the United States alone, nearly a million people visit their doctor at least once (National Center for Health Statistics-http: www.cdc.gov/ncds/fastats/docvisit.htm). The average patient visits a doctor 3.1 times per year. The most frequent principal reason for the visit is a general medical examination, the most frequent diagnostic procedure performed is a blood pressure check, and the most frequent principal diagnosis is upper respiratory tract infection. Other diagnoses in the top 20 categories for which patients visit their doctor include diabetes, arthritis, asthma/bronchitis, sinus infection, etc.

A typical visit to the doctor's office involves the patient completing a questionnaire detailing demographics, insurance/financial or payment procedure, personal information (habits like smoking, occupation), past medical problems, family history, and the reason for the present visit. The physician or one of his/her staff asks the patient additional questions and records the patient's pulse, blood pressure and weight. The physician performs a visual examination of the patient, and may inspect the ears and throat, listen to their heart, lungs and abdomen with a stethoscope, feel the patient's body for enlargement of organs, accumulation of fluid in the body cavities, any lumps or tender spots, range of movements or restriction of various joints and a neurological exam, etc. The physician may then order laboratory investigations such as blood tests, EKG, X-rays, etc. Based on part or all of this database, the physician formulates a diagnosis and, if necessary, recommends a treatment which can be one or all of the following:

1. Medicines
2. Surgery
3. Physical therapy
4. Rest
5. Observation
6. Additional evaluation, consultations, diagnostic testing, etc.

Follow up visits for minor complaints such as a sore throat usually do not require thorough examination. Follow-up visits to reassess the effectiveness of blood pressure medicines or diabetic medicines typically involve a discussion and/or limited examination. Doctors usually maintain offices in expensive medical buildings, have staffs which command high salaries, have multiple phone lines and other overhead expenses which are ultimately all added to the patients' bills.

The patient or his or her legal-guardian typically makes an appointment to see the doctor days to weeks in advance, mostly at the doctor's convenience, leaves the home or office, drives several miles, misses work, tries to find a parking spot (which may not be available or gratis), and waits in the doctor's office before he or she is seen.

Most of the office visits, especially for follow up or for minor complaints, are very brief examinations with the physician, require an inordinate amount of time, and money is wasted in the process. Additionally, the driving back and forth and waiting may exacerbate the patient's condition.

Telemedicine is the use of electronic information and communication technology to provide and support health care when distance separates the participants.

A major drawback of the presently available telemedicine system is its set up cost, which are approximately $100,000 per site. At a minimum, there must be two sites, one for the patient and one for the doctor. Moreover, both the patient and the doctor have to travel to their respective telemedicine facility because the communication signals only begin and/or end at the facility and nowhere else. Furthermore, there are no mechanisms for integrating telemedicine into an existing physician practice to facilitate payment for telemedicine-based services.

There is, therefore, a need in the art for a mechanism which allows for a patient to contact a physician remotely and to receive medical services, wherein the arrangement of services between doctors and insurance companies is facilitated electronically and provides the ability for patients to submit diagnostic testing to a physician and to correspond with that physician, such that they can receive a diagnosis and treatment.

SUMMARY OF THE INVENTION

The present invention is a system and method for enabling patients, with equipment readily available off the shelf, to correspond in real-time with their physicians without the need for expensive facilities in remote locations. The present invention simplifies the material requirements by utilizing, for example, a personal computer (PC) equipped with a digital camera. Patients can use standard diagnostic equipment, such as a thermometer, stethoscope, etc. that are often kept at the home. The PC can be equipped with Internet connectivity and a web browser that can render web pages provided by a virtual clinic that establishes the connection between the patient and the doctor. The particular doctor is chosen by the virtual clinic based upon a variety of factors, including, but not limited to, time of day, availability of the patient's standard physician, type of medical condition, etc. The virtual clinic then provides the proper connectivity between the selected physician and the patient or otherwise enables them to communicate. The doctor can then instruct the patient to perform the necessary measurements and, through textual, image, audio and/or visual means, diagnose the problem and recommend appropriate treatment.

An exemplary embodiment of the present invention is directed to a method and system for establishing a virtual clinic. Specifically, a virtual clinic is created by establishing communications and working relationships with patients, physicians, and insurance companies to facilitate the remote diagnosis and treatment of patients. In the first exemplary embodiment, a patient may contact his/her insurance carrier via a web page on the Internet. The insurance company then matches the patient to one of its plans and then forwards information to the virtual clinic, which then responds to the patient's web request. The patient is then put in operative communication with a physician that is known by the virtual clinic to be licensed to practice medicine in the patient's current location and to have expertise in the patient's condition.

Another exemplary embodiment of the invention is directed to a method for a patient to contact remotely a physician and to receive medical services from that physician. The method includes the steps of: the patient contacting a virtual clinic via a wide area network such as the Internet; the patient providing information on his or her medical condition; the virtual clinic identifying automatically a physician based on the patient provided medical condition information; the patient corresponding with the physician; the patient submitting diagnostic testing to the physician; and the physician informing the patient of the treatment.

The present invention provides a method and system to diagnose and treat certain ailments without the patient ever leaving his/her home or place of work and without the doctor needing an office. The present invention thus provides tremendous savings for the patient (precluding the need for driving and loss of time at work, etc.) and for the doctor (precluding the need for an expensive office), in addition to the convenience and increase in productivity.

The invention relates to a virtual clinic, which allows remotely located physicians (or other professionals) to perform medical examinations and consultations with remotely located patients (or clients). Patients access the physicians (and vice-versa) using the virtual clinic which allows the parties to interact via a wide area communication network such as the Internet, or other electronic, satellite, or digital media, or other type of remote consumer business-to-business communication system. The virtual clinic can provide secured access, pre-established contracts to perform professional services, appointments, referrals, and any other information or service to facilitate interaction between patients and physicians. The virtual clinic provides for the input, storage, manipulation, and retrieval of patients' medical records or data, and can also store notes from the physician for future reference by the same or a different physician. The virtual clinic may also provide medical and electronic equipment at remote sites for access and use by patients or others. The equipment may include computers (with access to a communication network), a camera or other means of recording and/or transmitting images, and medical equipment, such as thermometer, stethoscope, ultrasound machines, EKG machines, and other medical equipment. All equipment may have the capability to input and transmit data to the virtual clinic for storage, manipulation, access, or retrieval of the data by others. The present invention is equally applicable to other professionals, such as attorneys, accountants, etc.

In various embodiments, a user provides a request for a specialist to a virtual clinic. The request may include a request for medical services identifying medical needs. The user may then receive specialist information from the virtual clinic. The virtual clinic may establish real-time communication between the user and the specialist. The user may receive instructions from the specialist via the virtual clinic to perform a test. The user may then report a test result of the test to the specialist via the virtual clinic. The virtual clinic may receive and store a diagnosis from the specialist.

The method may further comprise storing locations of a plurality of diagnostic centers, storing a list of diagnostic testing equipment present at each different diagnostic center, generating a list of diagnostic centers from the plurality of diagnostic centers based at least in part on proximity to the user, and providing the list of diagnostic centers to the user. The list of diagnostic centers may also be based at least in part on the request for the specialist.

In some embodiments, the method may further comprise the virtual clinic receiving the user information and determining the specialist based on the user information.

The communication between the user and the specialist may be stored and access to the communication may be enabled to a third-party. In one example, the third-party is a trainee. In another example, the third-party is a peer.

In various embodiments, the method may further comprise establishing a real-time communication between the specialist and a consultant via the virtual clinic during the real-time communication between the user and the specialist. In some embodiments, the consultant does not have access to an identity of the user. Further, in some embodiments, the method may further comprise establishing a real-time communication between the specialist and a supervisor via the virtual clinic during the real-time communication between the user and the specialist.

A system may comprise a specialist device, a user device, and a virtual clinic device. The specialist device may be for use by a specialist and may be configured to receive user information from a virtual clinic, provide instructions to a user via the virtual clinic to perform a test, receive a test result from the virtual clinic, and provide a diagnosis of the user via the virtual clinic.

The user device may be for use by the user and configured to provide a request for the specialist to the virtual clinic and provide the test result to the virtual clinic. The virtual clinic device may be configured to provide specialist information to the user device and establish real-time communication between the specialist device and the user device.

Another method in various embodiments comprises providing a request for the specialist from a diagnostic center to a virtual clinic, establishing real-time communication between an administrator at the diagnostic center and a specialist via the virtual clinic, receiving instructions to perform a test with diagnostic test equipment operatively coupled with the diagnostic center, the instructions received from the specialist, and providing a test result from the diagnostic test equipment to the specialist via the virtual clinic.

The diagnostic center may be portable. The diagnostic center may be remotely located form the user's home and remotely located from a dedicated treatment facility. The administrator may not be medically trained.

In some embodiments, the user is an owner of a car, the specialist is a car mechanic, and the test is performed on the user's car. In other embodiments, the user is an owner of an animal, the specialist is a veterinarian, and the test is performed on the user's animal.

A diagnostic center may comprise a network interface, a communication interface, and diagnostic testing equipment. The network interface may be configured to communicate with a remote virtual clinic. The communication interface may be configured to establish real-time communication between an administrator at the diagnostic center and a specialist via the virtual clinic. The diagnostic testing equipment may be configured perform a test and provide a test result to a specialist over the virtual clinic.

Features and advantages of the invention will be apparent from the following description of the embodiments, given for the purpose of disclosure and taken in conjunction with the accompanying drawings.

BRIEF DESCRIPTION OF THE DRAWINGS

A more complete understanding of the present disclosure and advantages thereof may be acquired by referring to the following description taken in conjunction with the accompanying drawings, wherein.

Figure 1:
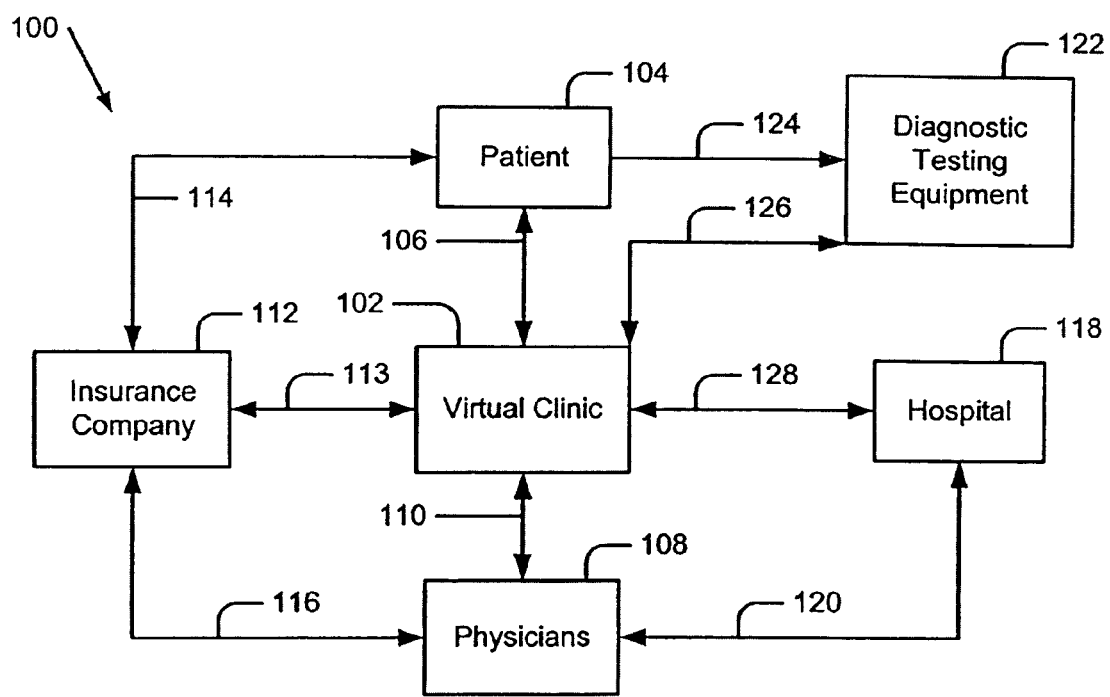
FIG. 1 is a schematic representation of the present invention showing the relationships between the virtual clinic and other entities.

While the present invention is amenable to various modifications and alternative forms, specific exemplary embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

The present invention is directed to a system and method for a patient to remotely contact a physician and receive medical services which utilizes a virtual clinic to contract with physicians and insurance companies and which facilitates the identification of, and contact with, a physician, based upon the patient's medical condition. The present invention enables the patient to submit to diagnostic testing and forwards the results to the physician who can then correspond directly with the patient.

As used herein, a "virtual clinic" is a professional association such as a corporation or partnership having a presence in a telecommunications media, such as, the Internet, that hires or otherwise contracts with physicians and/or insurance companies and provides services somewhat comparable to clinics or hospitals. The virtual clinic can be a hardware device that is connected to a suitable network, or a software program running on a computer system that is connected to the network, or any combination there between. The virtual clinic can be run autonomously, or it can have one or more human operators. Ideally, the virtual clinic is provided with circuitry and/or logic that enables the clinic to receive information from a patient and/or the patient's insurance carrier or employer in order to determine which of the physicians, nurses, nurses' assistants, physicians' assistants, or other medical personnel would be best able to handle the patient's request within legal limits.

Before the virtual clinic receives requests from patients, it first establishes contracts or other working relationships with one or more physicians and other medical personnel. Information, such as licensures, specialization, experience, hospital affiliations, etc. are stored by the virtual clinic and are used to match a patient's needs to the available medical personnel who are affiliated with the virtual clinic. Additional contracts or working relationships can be established between insurance carriers and/or employers in order to provide benefits to their insured or employees, respectively.

Once the virtual clinic establishes sufficient working relationships with physicians and/or insurance carriers and/or employers, it creates a presence on the network by, for example, creating a web page that enables a patient to request consultation with a medical professional. Similarly, an arrangement with an employer or insurance company can be established so that when a patient views his/her carrier's or employer's web site, the patient is forwarded to the virtual clinic's web site. Sufficient information can be transmitted during the forwarding process to identify either (or both) the insurance carrier/employer and the patient in order for the virtual clinic's response to be tailored as desired. Such tailoring can include the use of trademarks or style that is similar to the styling or trade dress of the first site visited by the patient. This is a useful technique to give the patient the impression that they are communicating with the correct (approved) web site.

Once the patient communicates his/her identifying information and medical complaint/condition, a human and/or machine associated with the virtual clinic can interpret the request and determine which medical professional should be consulted based on an appropriate set of criteria that can include, but is not limited to, the patient's current location (for legal licensure constraints), condition (for specialization), and time (availability of the medical professional within a time zone having those working hours). Once selected, the virtual clinic establishes communications with the medical professional (typically a physician) and then either coordinates the communications link between the physician and patient or simply tells the patient or physician how to contact the other party directly.

The virtual clinic can do more than simply facilitate communications. The virtual clinic can also store and retrieve patient information by a medical professional, insurance carrier or employer. Moreover, the virtual clinic can also facilitate the payment of fees and expenses incurred by the medical professionals in the course of caring for the patient. For example, after the medical professional and patient have concluded their visit, the physician can submit a bill to the virtual clinic which will then handle the bill on the physician's behalf with either the insurance carrier, the employer, or the patient.

In a first preferred embodiment, a virtual clinic establishes contracts or other working arrangements with physicians and patients (or patient's employers or patient's insurance company) to provide the service. The virtual clinic also establishes communication links between itself and the patients and physicians, typically through a wide area network such as the Internet. For example, patients can utilize their PC's at their home or at work to log on the web site of the business. An appointment time is given or the patient may request urgent care. The patient will sign electronically a consent to receive medical treatment and a contract to pay for the services. The virtual clinic can charge the patient's insurance company, or charge the patient directly for the service and reimburse the doctor for the doctor's portion. Alternatively, the insurance company may have an existing contract with the doctor in which case the insurance company will pay the virtual clinic for its portion of the service and handle the doctor's fees per the contract. In yet another embodiment, the doctor bills the patient directly and the doctor pays a fee to the virtual clinic as a specialist.

The virtual clinic advertises its services, provides a list of supplies needed at home or at the PC which the patient utilizes to be evaluated by the doctor (see list of "preferred equipment" below). It provides instructions on-line to the patient on the use of the various equipment and supplies. It provides the hardware and software necessary for patients to access them and be connected to the physicians.

The physician utilizes a PC, preferably with a computer camera or digital video camera and access to the Internet. He or she signs a contract with the virtual clinic to provide telemedicine services. He or she agrees to be available at specific hours or at any hour. He or she agrees to evaluate patients only by appointment or be available for patients needing urgent or emergency care without appointment. He or she may agree to evaluate only established patients or to accept new patients. The physician may be licensed to practice in one or more states, but would be limited to practice only in the state(s) in which he/she is licensed.

The virtual clinic maintains a list of the physicians with their specialties, their qualifications and relevant information (board certification, school and year of graduation, experience and expertise, etc.).

When a patient accesses the virtual clinic, he/she is asked to choose a physician from among those on their panel, or if the patient does not have a preference or needs urgent care and his/her personal choice is not available for providing urgent care, the virtual clinic connects him/her to an appropriate physician in the specialty which the patient is seeking.

Referring now to the drawings, the details of an exemplary embodiment of the present invention is schematically illustrated. FIG. 1 depicts an example of the relationships that the virtual clinic 102 has with other entities. The virtual clinic 102 serves patients 104 in a number of relationships 106. For example, the patient 104 supplies information about his medical condition to the virtual clinic 102 and the virtual clinic 102 selects an appropriate physician 108 who provides a diagnosis and treatment back to the patient 104 through the virtual clinic 102 through relationship 106.

The virtual clinic 102 also has a number of relationships 110 with physicians 108, for example, the virtual clinic 102 refers patients 104 to the physicians 108 through relationship 110.

The virtual clinic 102 also has relationships 113 with insurance companies 112, such as insurance companies 112 reimbursing the virtual clinic 102 for medical services arranged by the virtual clinic 102.

The patients 104 may have existing relationships 114 with insurance companies 112, such as a group insurance policy. Physicians 108 may also have relationships 116 with insurance companies 112, such as physicians 108 providing discounted medical services upon referrals by insurance companies 112. Physicians 108 may also have relationships 120 with hospitals 118, such as privileges at certain hospitals 118.

The virtual clinic 102 may have relationships 128 with at least one hospital 118, for example, the virtual clinic 102 may contract with one or more hospitals to provide diagnostic testing to the virtual clinic or to provide medical services which require the patient's presence (e.g., stitches, setting broken bones, etc.).

The present invention is useful with equipment that is readily available off-the-shelf. For example, a personal computer (PC) equipped with a digital camera can be used to transmit images from the patient to the doctor. Patients can use standard diagnostic equipment, such as a thermometer, stethoscope, etc. that are often kept at the home. It is preferred, however, that the patient have at their home a digital thermometer and digital stethoscope that can input real-time data into a PC for immediate use by the physician or other medial professional. The PC or other communication device can, for example, be equipped with Internet connectivity and a web browser that can render web pages that are provided by the virtual clinic. Based upon information uploaded by the patient, as well as an optional comparison with patient information retrieved from a database, the time of day, the availability of the patient's standard physician, the type of medical condition, etc., a particular doctor is selected by the virtual clinic. The virtual clinic then provides the proper connectivity between the selected physician and the patient or otherwise enables them to communicate. The doctor can then instruct the patient to perform the necessary measurements and, through textual, image, audio and/or visual means, diagnose the problem and recommend appropriate treatment.

While the present invention can work with the equipment mentioned above, it is envisioned that some patients with chronic conditions such as diabetes, will have purchased additional equipment not found in most households. This diagnostic testing equipment can itself contain telecommunications/Internet connectivity to facilitate the uploading of test results to the physician via the communications link established by the virtual clinic. Preferably, diagnostic testing equipment 122 is in communication 126 with the virtual clinic 102, such that patients 104 can access 124 the diagnostic testing equipment 122 and submit the diagnostic testing results to the virtual clinic 102 through communication 126 and ultimately to physicians 108.

Figure 2:
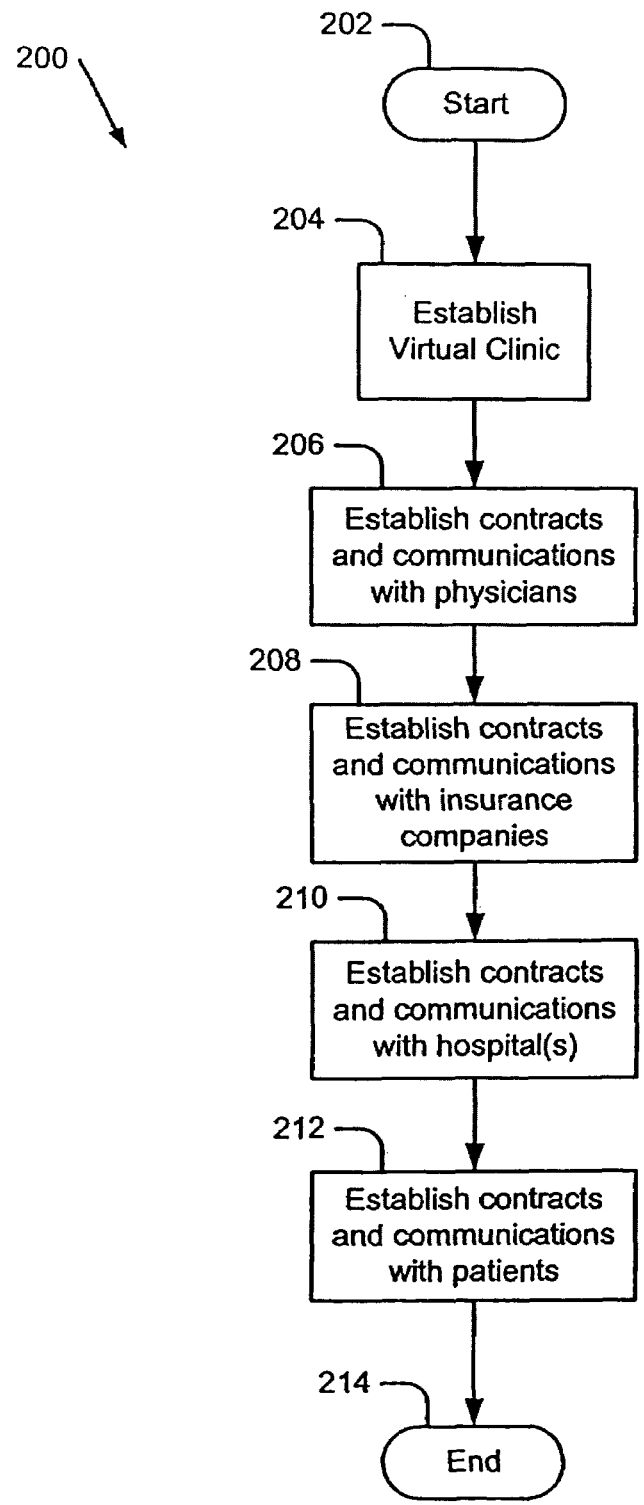
FIG. 2 is a schematic representation showing the establishment of contracts between the virtual clinic and other entities.

Referring now to FIG. 2, the method of the present invention starts out generally at step 202. Initially, a virtual clinic is established, step 204, and this generally may be any known virtual clinic such as a corporation or partnership. The virtual clinic establishes a working relationship, often in the form of a contract or other obligation, with physicians, step 206, to provide medical services to one or more patients. The virtual clinic establishes contracts with insurance companies, step 208, to, for example, reimburse the virtual clinic for medical services provided to the patients. The virtual clinic may establish contracts with one or more hospitals, step 210, to provide diagnostic testing or medical services which require the patient's presence. The hospital of step 210 can be a standard hospital, however, it is envisioned to encompass not only hospitals but may also include a standard clinic, a laboratory, or other diagnostic/treatment facilities that provide technical services and/or equipment not found in the patient's home. The virtual clinic also establishes contracts with patients, step 212, such that the patient will provide payment in return for receiving medical services. Here, the payment may be authorization of the insurance company to pay all or part of the fee for the medical services or the patients may directly pay the fee for the medical service and possibly request reimbursement from the insurance company.

Figure 3:
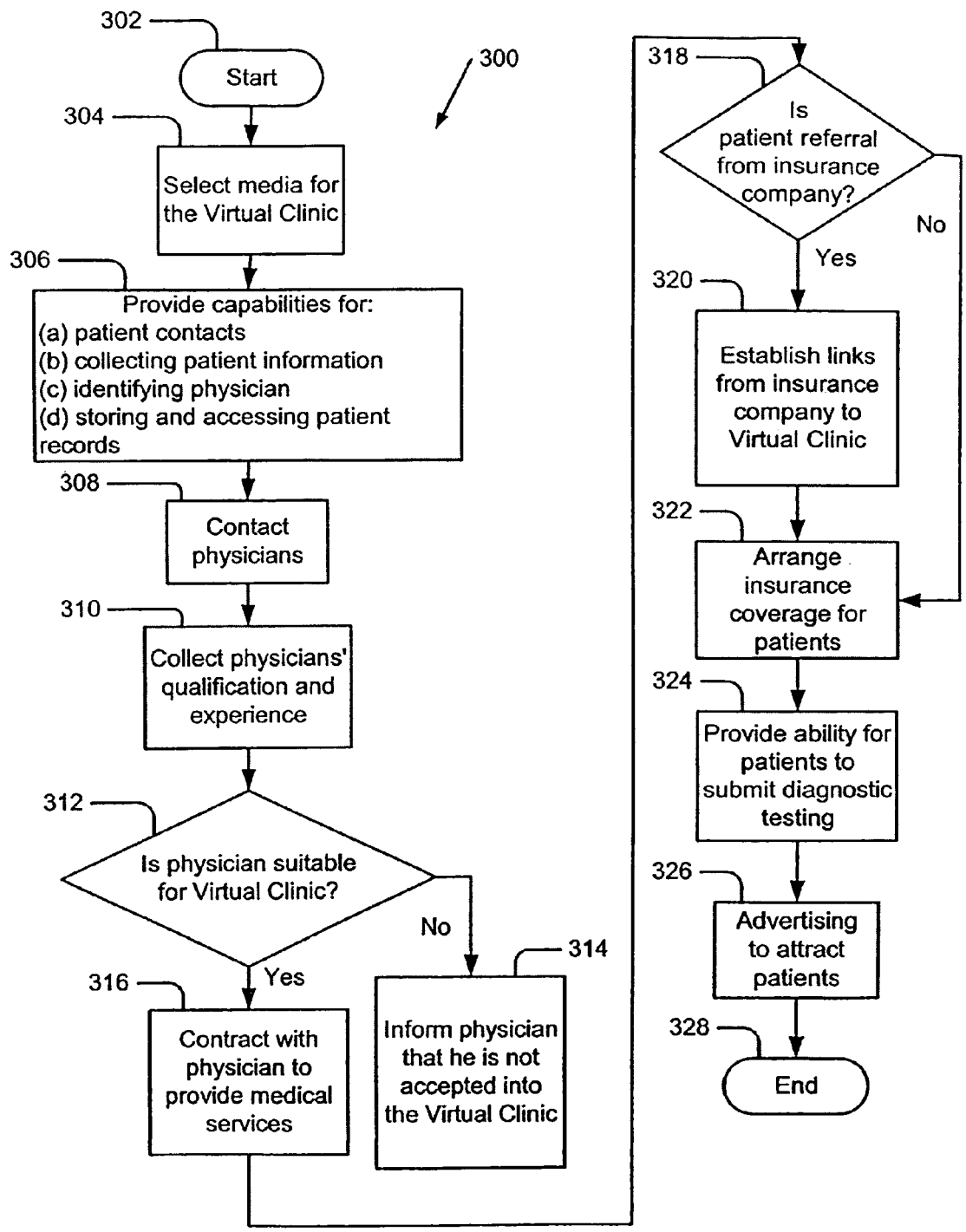
FIG. 3 is a flow chart of an embodiment of the present invention showing the development of a virtual clinic for allowing a patient remotely contacting a physician and receiving medical services.

Referring to FIG. 3, the flow chart 300 shows an embodiment of the present invention showing the development of a virtual clinic. The method starts out generally at step 302. First, a media is selected for the virtual clinic, step 304. Preferably, the media is the Internet and the virtual clinic is represented on an Internet site and has Internet connections to, for example, physicians, insurance companies, a hospital, clinic, laboratory, or other diagnostic facility, and allows patients to access the Internet site directly or may allow insurance companies to electronically tie to the virtual clinic's site. The media may also be a phone system, for example, an automated phone system.

Preferably, the virtual clinic has a combination of hardware and software which provides capabilities for:
   (a) patient contacts;
   (b) collecting patient information;
   (c) identifying physician based on patient's submitted information on his or her medical condition; and
   (d) storing and accessing patient records, step 306.

The virtual clinic contacts physicians, step 308, and collects qualifications and experience, step 310. Preferably, the virtual clinic determines whether the physician is suitable for providing medical services for patients referred by the virtual clinic, step 312, and if not, the physicians are informed that they are not accepted into the virtual clinic, step 314. If the physicians are suitable for the virtual clinic, a contract, partnership, or other working relationship is entered into between the physician and the virtual clinic, providing that the physician will provide medical services to patients referred to it by the virtual clinic, step 316. In addition to contracting with physicians, the virtual clinic may also contract or partner with other organizations, such as hospitals, clinics (both inpatient and outpatient), laboratories, and other diagnostic/treatment facilities.

As noted above, patients may be referred to the virtual clinic from a number of sources, including referrals from insurance companies. Preferably, the virtual clinic determines if the patient referral is from an insurance company, step 318, and if so, an attempt is made to establish links from the insurance company to the virtual clinic, step 320. If not, preferably, steps are taken to arrange insurance coverage for the patient, step 312.

Hardware, software, and equipment is preferably provided to provide the ability for patients to submit diagnostic test results to physicians, step 324. Preferably, the virtual clinic advertises to attract patients, step 326. The advertising may be directed at individual patients or may be directed at insurance companies to refer patients to the virtual clinic, for example, by providing lower cost medical services for the insurance company's benefit.

The preferred equipment for use in conjunction with the preferred virtual clinic may include:
1. A personal computer;
2. Access to the Internet;
3. Digital video camera or computer camera in operative communication with the computer;
4. Weighing machine;
5. Thermometer;
6. Electronic pulse, blood pressure, pulse oximeter, stethoscope, home blood sugar monitoring apparatus, if appropriate;
7. Digital scope for viewing mouth and external ears;
8. EKG machine, if appropriate;
9. Compact portable ultrasound equipment, if desired; and
10. Any other equipment as may become available in the future within the financial reach of the average family.

In addition, some families may have other equipment at the home if they have a family member with a chronic condition. For example, patients with diabetes may have additional equipment in the home for testing blood sugar levels that would not be found in the average home. For purposes of this disclosure, it is envisioned that any of the additional equipment for these chronic conditions, whatever they are, may be equipped to communicate on the same or other channels available to the patient and can be utilized by the patient, the physician, and the virtual clinic to provide additional diagnostic information.

Most of these, except items no. 9 and 10, are available and relatively inexpensive. Item no. 6 is typically purchased as a single pack, and several of these instruments could be packaged into a single device (see U.S. Pat. No. 5,701,904) which can be directly connected to an inlet port in the PC. Preferably, the virtual clinic provides a way for the physician to determine what diagnostic testing equipment is available to the patient, either at the patient's home or at a conveniently located public facility. While the patient should know what diagnostic testing equipment exists at his residence, and can enter this information upon being prompted, he may not appreciate what equipment exists at nearly public facilities. In this case, the virtual clinic may keep track of the diagnostic testing equipment located at public facilities, and use, for example, zip codes to determine if the public facility is near the patient.

Figure 4:
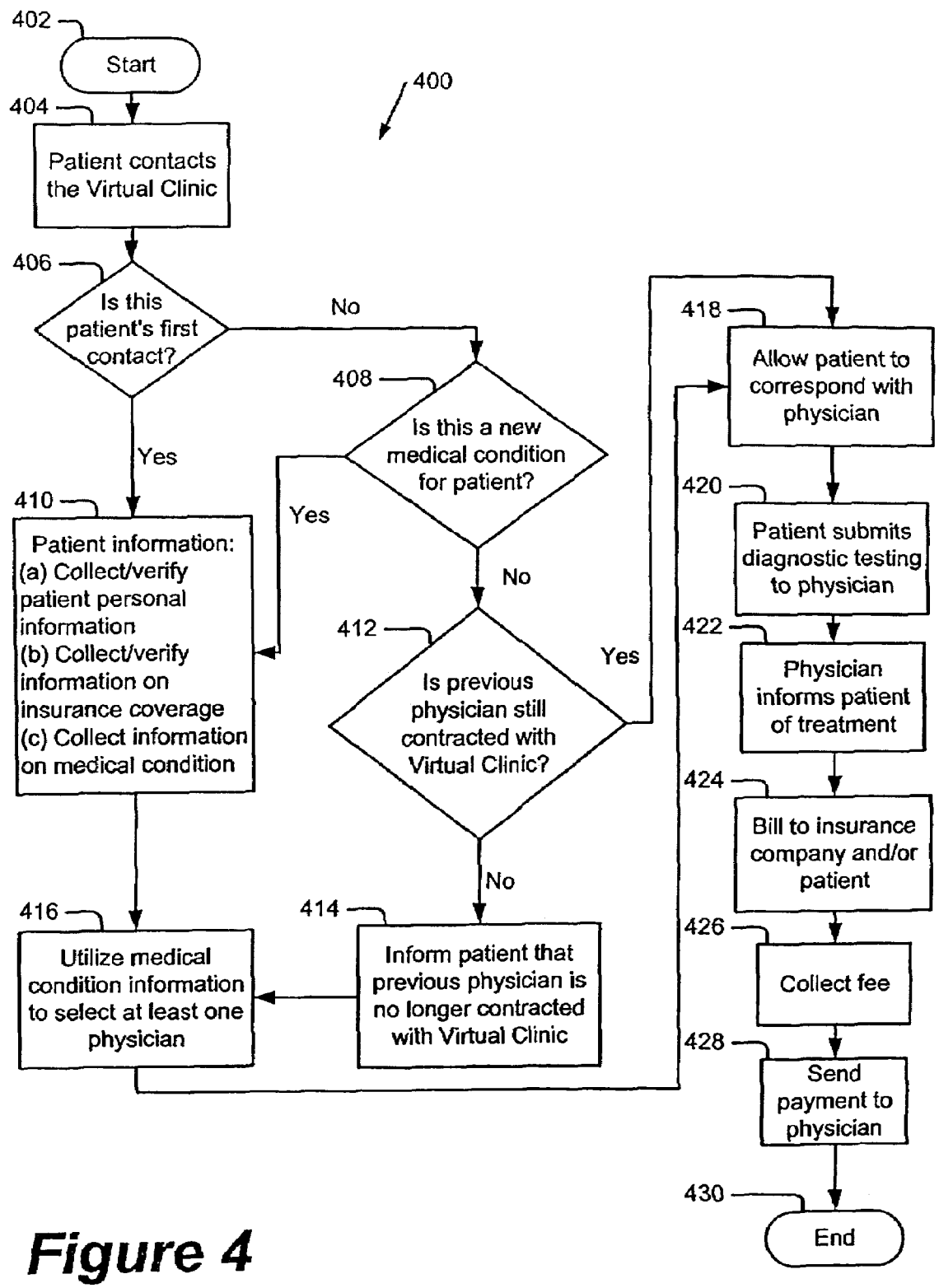
FIG. 4 is a flow chart of an embodiment of the present invention showing a method for a patient remotely contacting a physician and receiving medical services.

FIG. 4 shows a flow chart 400 of an embodiment of the present invention. The method starts out generally at step 402. The patient contacts the virtual clinic, step 404, and this may be through a direct contact or may be a referral through an insurance company. Preferably, a questionnaire is provided which asks whether this is the patient's first contact with the virtual clinic, step 406. If it's not the patient's first contact, then the patient is questioned about whether he has a new medical condition, step 408. If either it is the patient's first contact, step 406, or the patient has a new medical condition, step 408, then the patient provides additional information such as:
   (a) collect/verify (if existing patient) patient personal information;
   (b) collect/verify information on insurance coverage; and
   (c) collect information on medical condition. Step 410.

If the patient is an existing client, step 406, and is receiving continuing treatment for a medical condition, step 408, then, preferably, a determination is made whether the previous physician is still contracted with the virtual clinic, step 412. If not, the patient is informed that his previous physician is no longer connected with the virtual clinic, step 414, and the patient's information regarding his medical condition is used to select at least one other physician to provide the patient with medical services, step 416. If the patient's previous physician is still connected with the virtual clinic, step 412, or the patient receives a new physician pursuant to step 416, then the patient is allowed to correspond with the physician, step 418, and submit diagnostic testing to the physician, step 420, such that the physician may inform the patient of treatment, step 422.

The virtual clinic submits a bill to the insurance company and/or the patient, step 424, and the virtual clinic collects the fee for the medical services from the insurance company and/or patient, step 426, and a portion of this fee is sent to the physician, step 428.

Figure 5:
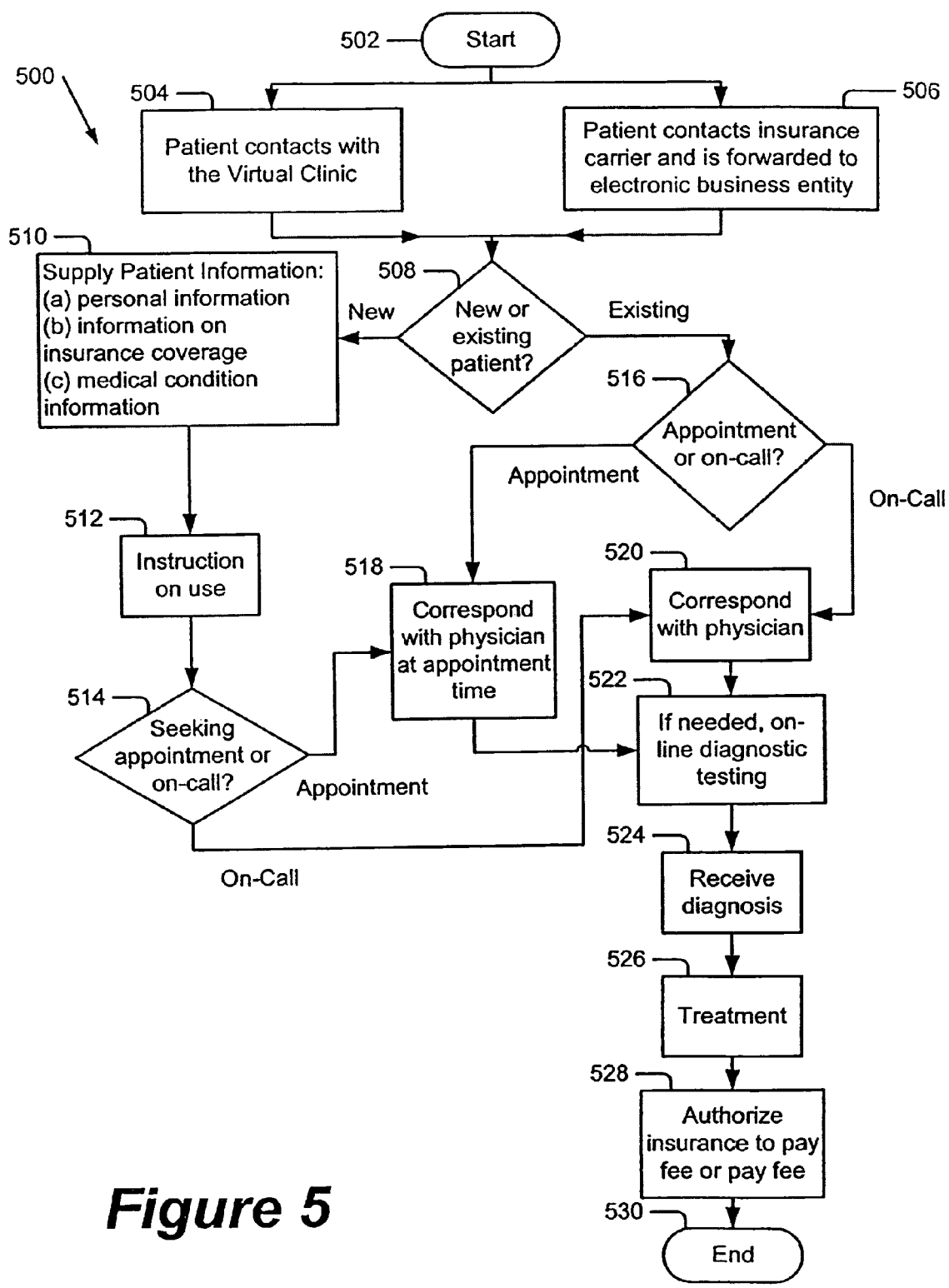
FIG. 5 is a flow chart of an embodiment of the method of the present invention from a patient's perspective.

FIG. 5 is a flow chart 500 of an embodiment of the method of the present invention from a patient's perspective. The method starts out generally at step 502. The patient may contact the virtual clinic directly, step 504, or the patient may contact an insurance carrier and be forwarded or otherwise referred to the virtual clinic, step 506. Alternatively, the patient may approach the virtual clinic after being directed to do so by word-of-mouth advice from friends or family for which the virtual clinic may receive a finder fee or partial payment from the physician. Additionally, the virtual clinic may attract patients directly through advertisement, preferably on the Internet, by placing adds with insurance carriers, laboratories, household equipment manufacturers, employer, famous web portals, and web sites that cater to people seeking medical advice or medical attention for which the virtual clinic can pay the site owners for the "click-through." The way in which the patient learned of the virtual clinic can be optionally verified when the patient is questioned regarding whether he/she is a new or existing patient, step 508, and if a new patient, then the patient is asked to supply patient information, including:

(a) personal information;
(b) information on insurance coverage; and
(c) medical condition information, step 510.

If the patient is new to the virtual clinic (under step 508), then the patient is provided instructions on the use of the system, step 512, and is questioned regarding whether he/she is seeking an appointment or wishing to converse with a physician on-call, step 514.

Referring back to step 508, likewise, if the patient is an existing patient, he is questioned whether he seeks an appointment or an on-call contact with a physician. From step 514 and step 516, if a patient wishes to correspond with physician pursuant to an appointment, an appointment is set up through the virtual clinic with both the patient and physician, such that the patient may correspond with the physician at the appointment time, step 518. If from step 514 or step 516 the patient wishes to converse with a physician on-call, then the patient's information on his/her medical condition is used to determine a suitable physician and the virtual clinic determines whether that physician is on-call at that time. If the physician is on-call, the patient may correspond directly with the physician, step 520. If needed, the physician and patient may conduct on-line diagnostic testing, step 522, then, the patient receives a diagnosis, step 524, and the physician recommends a treatment, step 526. Next, arrangements are made for the patient to authorize the insurance company to pay the fee for the medical service or for the patient to pay the fee directly, step 528.

Figure 6:
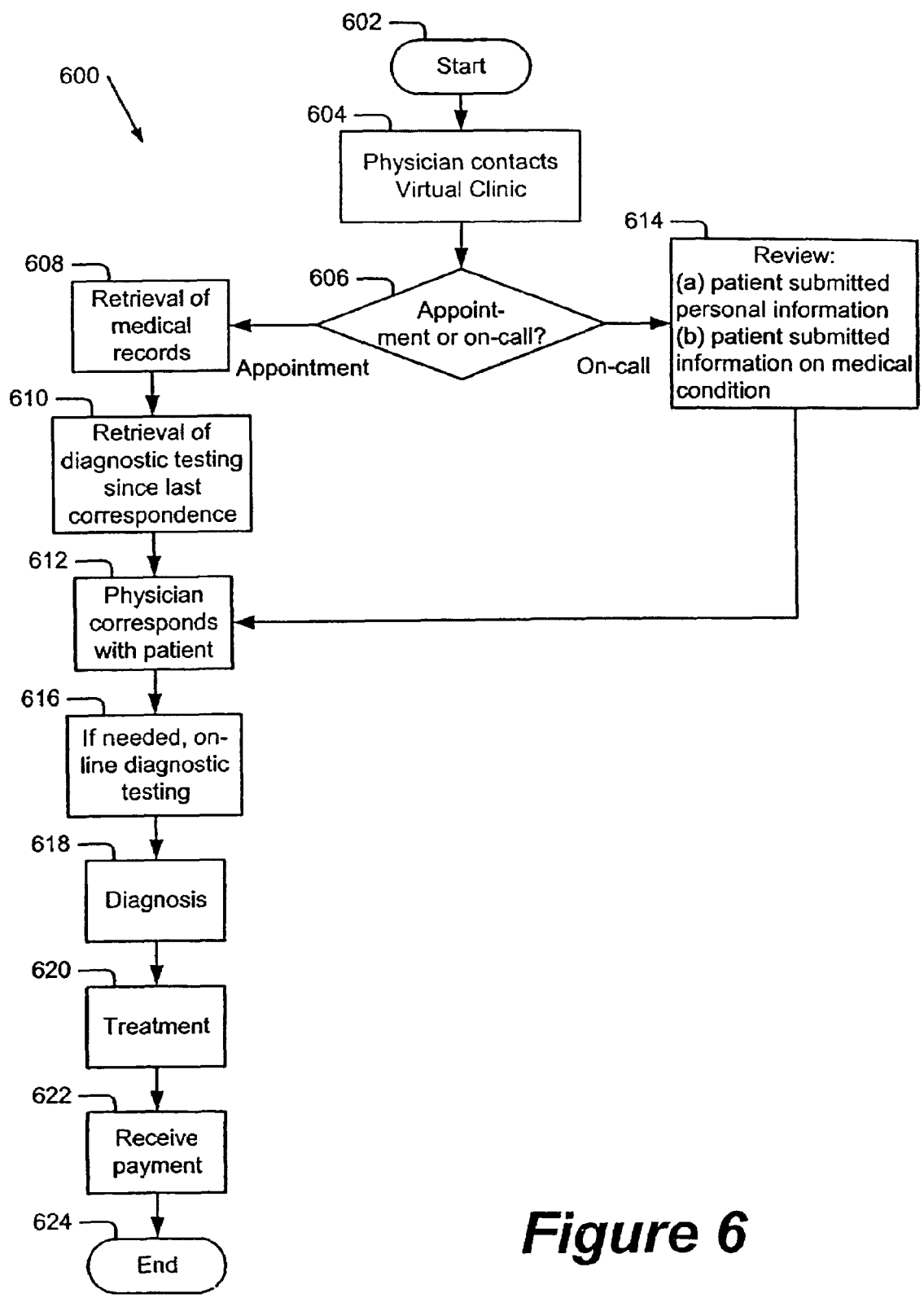
FIG. 6 is a flow chart of an embodiment of the method of the present invention from a physician's perspective.

FIG. 6 shows a flow chart 600 of an embodiment of a method of the present invention from a physician's perspective. The method starts out generally at step 602. Initially, the physician contacts the virtual clinic, step 604, informing the virtual clinic whether he is going on-line to conduct an appointment or is available for on-call conferences, step 606. If the physician is conducting an appointment, he may first retrieve the patient's medical records, step 608, and retrieve any diagnostic testing since his last correspondence with the patient, step 610, and then correspond directly with the patient, step 612. If the physician is on-call (from step 606), before corresponding with a patient, step 612, he may first review the patient-submitted personal information and the patient-submitted information on his/her medical condition, step 614, such that the physician may more thoroughly address the patient's concerns. If needed, on-line diagnostic testing may be conducted, step 616, a diagnosis is made by the physician, step 618, the physician recommends treatment, step 622, and, after the virtual clinic receives its payment, it forwards a payment on to the physician, step 624.

An embodiment of this invention includes a virtual clinic comprising an electronic network system providing services between professionals and clients. A preferred embodiment includes such a virtual clinic for providing medical services. Another embodiment includes on-site monitoring and testing in conjunction with the virtual clinic. Yet another embodiment includes associated services such as insurance coordination and appointments in conjunction with the virtual clinic.

A preferred embodiment is an Internet-based system. The virtual clinic could operate nationally and could have a physician in California treat a patient in New York as long as the physician has a New York state license. The advantage would be that the physician could be working at 4:00 p.m. California time (regular work time) while the patient would be at home at 7:00 p.m., New York time, a difficult, if not impossible time to find a physician for a regular follow up visit to review a change in medicine for diabetes.

The patient and physician are able to see each other via a camera hooked up to their PCs and can communicate directly with each other verbally or by typing on their respective screens.

When the patient is placed in contact with his or her doctor, the doctor may have a prepared screening questionnaire on the Internet which the patient completes, providing details of the nature of the problem, relevant past and family medical history, medications the patient is taking, any known drug allergies, etc. The doctor may choose to have a separate consent for treatment and payment form signed electronically by the patient.

The physician or his/her nurse, PA, etc., would review the questionnaire completed by the patient and ask any additional relevant questions. The physician would then direct the patient to weigh, to record his/her temperature, and to place his/her finger in the digital blood pressure/pulse recording device (vital signs recording). The physician can view the patient and see if he/she is in pain, short of breath or otherwise uncomfortable, or appears anxious, depressed, etc. The physician or physician's assistant could ask the patient to place the digital electronic scope to view the oral cavity (mouth) and inside the ear canal. The physician or physician's assistant would then require the patient to place the electronic stethoscope over different points of his/her body (heart, lungs, abdomen) directing the patient to breathe or hold his/her breath as appropriate (perform telecommunication). A family member or friend at home or at a place of work could easily assist with placement of the stethoscope in different positions as directed by the physician (perform tele-examination). The virtual clinic would provide audio/video instructions for above both on the Internet and by mail to the patients.

The virtual clinic could provide slightly more elaborate, but still relatively inexpensive set-ups with EKG, spirometry and compact portable digital ultrasound devices in places of work or any other remote location (where it would be cost effective for the employer rather than have loss of worker's time visiting a doctor). Additionally, employers, apartment complexes, homeowners' associations, etc. may set up a designated room suitably equipped for use with the virtual clinic that is accessible to members who do not have a PC at home. Patients themselves can add extra diagnostic equipment to their homes that supplement the diagnostic phase, particularly for patients with chronic conditions where the expense of the extra equipment can be readily justified.

The physician, with the data obtained, could order appropriate medication which could be called or faxed or e-mailed to a pharmacy. The virtual clinic may provide an electronic pharmacy service offering the best price on the medicine prescribed for the patient if the patient chooses, or the virtual clinic may maintain a licensed pharmacy to dispense medicines to the patient.

The physician may order laboratory or radiological imaging investigations via the virtual clinic. An order for the tests could be electronically communicated directly to the appropriate facility. The patient could set up a mutually convenient time with the facility to have the tests run. The laboratory or imaging facility will electronically communicate the results to the physician and electronically load imaging films taken on digital format for physicians to review and share with the patient, as necessary. The physician could set up a follow up visit with the patient through the virtual clinic to explain the results of tests, advise appropriate corrective measures, medications, if necessary, and provide educational material to the patient on the wide area network (e.g., aerobic exercise for reduction of lipids (fats) in the blood or specific exercises for back strain). The physician could have educational material available electronically or direct the patient to a web site from which the patient can print them on his/her printer.

The physician may require the patient to come into the office in person for a more detailed examination or refer the patient to a specialist.

Several other examinations can be performed on the patient including, but not limited to, the evaluation of the following: skin abnormalities through digital video camera, patient's gait by requesting patient to walk, swelling of joints, movement or restriction of joints, and tender spots by asking the patient to press on different parts of the body and reporting any tenderness, weakness in either side of the body by asking the patient to lift weights, coordination by viewing patient's handwriting, etc.

More sophisticated tests, such as visual field examination for screening for glaucoma can be done (see U.S. Pat. No. 6,033,076). A diabetic patient may monitor blood sugar at home and enter the data either through the virtual clinic's web site or physician e-mail which the physician may access at his/her convenience and inform the patient electronically of any adjustment in doses or medicine, change in diet, or activity recommendations, etc. The virtual clinic can also be equipped with circuitry and/or software that can monitor and/or compare the results of diagnostic tests that the patient (or a laboratory, etc.) uploads to the virtual clinic and, if necessary, analyze the uploaded data by, for example, comparing the test results to pre-determined limits set by the physician and/or against pre-set values or the patient's past values that can be stored in a database that is accessible to the virtual clinic. If the new test values falls below a minimum value, or exceeds a maximum threshold, the virtual clinic can issue a signal to the patient's physician or to an on-call physician or other medical specialist to prompt follow-up care for the patient. The virtual clinic can be equipped with circuitry and/or software that stores the pre-set limits by the physician or by generally accepted levels set by another organization (such as the American Medical Association). For example, referring to FIG. 1, the patient 104, the diagnostic test equipment 122, and/or the hospital/clinic/laboratory 118 could upload diagnostic information (temperature, blood test results, etc.) to the virtual clinic 102 by the communication channels 106, 126, 128, respectively. The virtual clinic 102 could be provided with a database internally, or it could access another database at, for example, the insurance company 112 or the hospital/clinic/laboratory 118. The uploaded data is then compared to the pre-set values (either pre-selected by the physician, an organization, and/or the patient's previously determined values) and, if the difference between the pre-set values and the uploaded values is higher or lower than a pre-determined threshold, a signal can be issued by the virtual clinic 102 to the physician 108 via communication channel 110. Incidentally, the physician 108 need not be the patient's personal physician, it can be an on-call physician (optionally determined by the virtual clinic) or other medical specialist such as a physician's assistant, nurse, nurse practitioner, technician, social worker, etc.

With the virtual clinic doctors do not have to maintain traditional office hours, as they could evaluate patients electronically from home, vacation spots, or at non-traditional hours or days of the week. Similarly, patients do not have to maintain traditional hours for routine office visits. If the diagnostic equipment is carried by the patient (such as a heart monitor), the recorded or real-time information can be uploaded automatically to the virtual clinic for analysis and forwarding of results (either normally or as part of an alert message) to the physician 108.

The doctor may be in a different time zone as long as he has a license to practice in the state where the patient is located, thus making it convenient for patients to visit doctors late in the evening, for example, a doctor in California at 4 p.m. Pacific time could consult with a patient located in New York at home at 7 p.m. Eastern time. They could, in fact, be in different countries as long as they are appropriately licensed. This would also expand the scope of practice for U.S. physicians who could advise and consult with patients outside the U.S. where the availability of medical services, especially experts, is severely limited or co-consult with an expert outside of the U.S.

Another advantage of the system is, if a patient cancels or does not log-on for appointment, the next one can be serviced immediately, electronically (as opposed to another patient driving to the doctor's office, which is not practical, given the time constraints). There would be no weather-related cancellations. Additionally, if the doctor is delayed, the patient may attend to other things at home or work.

The physician's assistant (PA, nurse, etc.) could perform a physical exam and store the data in an electronic format for the physician to review later, and the practitioner then advises the physician's assistant. Additionally, the physician's assistant could follow a preset protocol, such as obtaining certain diagnostic tests if the patient's temperature is greater than 101 degrees Fahrenheit.

The virtual clinic would maintain medical records and forward them, at the patient's direction, to any physician or consultant whom the patient identifies. As these records would be electronically stored and accessible, there would be a seamless transfer of data to another physician or consultant, if needed. If a patient sees a different physician at different times or needs to see multiple consultants, all of them would have access to the information simultaneously (much better than the present systems of carrying copies of charts) or would be able to interact with or without the patient simultaneously. Of course, security and confidentiality would have to be considered and incorporated into the system and all legal requirements satisfied. The physician could maintain a copy of all records and data for his/her personal files. A patient could also maintain his/her records in a CD format. In the event that a physician retires and no longer participates in the virtual clinic, the patient's information can easily be retrieved from memory and given to the patient and/or another physician who is or is not a virtual clinic-affiliated physician.

The virtual clinic is intended to operate as a for-profit virtual clinic. There are several ways in which the virtual clinic can make profits. Preferably, the virtual clinic receives payment directly from the insurance company or patient and then retains a percentage and forwards the remainder on to the physicians. Of course, the virtual clinic's retained percentage must cover its cost, such as maintaining an Internet-based system and, possibly, purchasing and maintaining diagnostic testing equipment located in publicly accessible areas and used for groups. Also, the virtual clinic could promote paid advertising for health and medical related products and services.

In an alternate embodiment, the physician may provide all of these services on the net without the intervention of an e-virtual clinic and charge appropriately for the services he/she provides. In this set up, the patient would access a physician's web site through which the physician or his/her assistant can guide the patient to the appropriate questionnaires and evaluation by the physician at a mutually convenient time after proper consents for treatment and payment have been completed.

In various embodiments, a virtual clinic is a software program (e.g., online application, a web site, or accessible at a web site) accessible over a network such as the Internet. The virtual clinic may comprise any number of applications and databases. Further, the virtual clinic may be hosted on a single computer or multiple computers. For example, a patient may access the virtual clinic via the Internet at a particular web address hosted by a web server (i.e., a virtual clinic device). One or more databases of the virtual clinic, however, may be located on one or more different computers apart from the web server.

In some embodiments, the virtual clinic stores specialist information regarding one or more specialists (e.g., physicians and other medical personnel) who may provide services through the virtual clinic. The specialist information may include information regarding the specialist such as licenses, specialization, experience, hospital affiliations, location of the specialist, availability, whether the specialist is currently on-call, and the like.

Further, the virtual clinic may store user information regarding one or more users. For example, the virtual clinic may store a user's (e.g., a patient's) health records and contact information.

Various embodiments and applications are possible. In one example, a patient accesses the virtual clinic and submits a request for a specialist. A request for a specialist may include a request for medical care. The patient may provide their medical care needs to the virtual clinic as well as any insurance carrier information that may be associated with the patient as a part of the request for the specialist.

The virtual clinic may provide the patient a selection of specialists. The provided selection of specialists may be generated by the virtual clinic based on the patient's medical needs (e.g., from the request for the specialist), specialist information, and/or any insurance carrier information or any combination thereof. For example, the virtual clinic may generate a list of physicians who are available to communicate over the virtual clinic, are specialist for the patient's medical need, and are covered by the patient's insurance carrier.

The virtual clinic may store carrier information regarding one or more insurance carriers that may provide or receive services through the virtual clinic. The carrier information may include contact information regarding insurance carriers, policies, billing information, and the like.

In some embodiments, the virtual clinic establishes a real-time communication between the physician (i.e., the specialist) and the patient. The communication may include text, images, audio, and/or video. For example, the virtual clinic may establish an electronic real-time communication between the physician and the patient such as VOIP, streaming video, chat, instant messaging, and the like. In some examples, the patient and physician using the virtual clinic may be able to see each other via a camera hooked up to their PCs and can communicate directly with each other verbally or by typing on their respective screens. In other embodiments, the virtual clinic provides the user's or the physician's contact information such that one party can contact (e.g., email, text message, or telephone) the other party.

During real-time communication through the virtual clinic, the physician may ask the patient questions, direct the patient to perform tests, perform an examination, and/or perform a diagnosis. For example, the physician may direct the patient to take a temperature or to operate test equipment (e.g., a machine for testing the patient's blood sugar). The patient may then provide the test results to the physician. In some embodiments, the test equipment may provide the test results directly to the physician via the virtual clinic. Those skilled in the art will appreciate that communication may be between a patient's caregiver (e.g., nurse, attendant, parent, spouse, or nanny) and medical personnel (e.g., physician, nurse, medical assistant, or paramedic). In one example, a physician may direct a patient's caregiver, such as a technician, to draw blood, obtain x-rays, and the like.

It will be appreciated by those skilled in the art that the patient (i.e., user) and physician (i.e., specialist) may be located in different states or even countries. Similarly, a device the runs all or part of the virtual clinic may be located anywhere network access is available. In one example, a patient in England may confer with a specialist in the United States over a virtual clinic being run in Germany.

The specialist may record patient data with the virtual clinic. Patient data is any data related to the patient (e.g., the name of patient, medical records, facts related to the examination, facts related to the diagnosis, impressions, or analysis). In one example, the virtual clinic formats an electronic document that the specialist may complete. The information within the electronic document and/or the document itself may be stored by the virtual clinic. It will be appreciated by those skilled in the art that the electronic document may be generated and/or formatted by the virtual machine device or the specialist device (discussed herein).

The virtual clinic may also include best standard of care guidelines. In one example, the guidelines are instructions that the physician, patient, insurance company, or any combination thereof, may consult when reviewing a patient's treatment options. In another example, the virtual clinic is configured to review medical records, monitor the session between the physician and patient, and automatically provide suggestions based on a pre-programmed standard of care. Embodiments of the virtual clinic may cooperate with systems implementing embodiments described in U.S. nonprovisional patent application Ser. No. 09/760,917, entitled "Computer System for Assisting a Physician," filed Jan. 16, 2001, which is hereby incorporated by reference.

In various embodiments, the virtual clinic and/or the specialist may direct the patient to a diagnostic center. In one example, the virtual clinic provides the location of various available diagnostic centers. The virtual clinic may also provide driving directions to the diagnostic center closest to the patient.

In some embodiments, the virtual clinic generates a list of available diagnostic centers based on the medical needs of the patient or input by the physician. For example, the physician may identify needed diagnostic testing equipment and provide those needs to the virtual clinic. The virtual clinic may then generate a list of diagnostic centers that have the desired diagnostic testing equipment. The virtual clinic may display a list of available diagnostic testing equipment for each available diagnostic center to the patient and/or physician.

At the diagnostic center, a user, such as an administrator of the diagnostic center, may access the virtual clinic and request medical care (and/or a specialist) for the patient. The administrator is any person who operates diagnostic test equipment. The diagnostic test equipment is in communication with the diagnostic center. The administrator may be medically trained (e.g., a physician, a nurse, a medical assistant, or a paramedic) or not medically trained.

The virtual clinic may establish real-time communication between the administrator and the specialist (e.g., a physician). At the direction or with the request of the physician, the administrator may operate the diagnostic test equipment. The test results of the diagnostic test equipment may be provided to the virtual clinic which may, in turn, provide the test results to the physician. In some embodiments, the test results of the diagnostic test equipment are provided directly to the physician, the patient, the administrator, or any combination thereof.

The virtual clinic may be configured to provide real-time images (e.g., video) and audio from the diagnostic centers to a remotely located physician. For example, an endoscopy procedure may be performed at the diagnostic center, whereby still or moving images with or without sound may be transferred via the virtual clinic to the physician who is watching the procedure in real time. The physician may also communicate with the person (e.g., administrator of the diagnostic center or the patient) conducting the test while the test is being performed to allow the physician to obtain needed information to perform an examination and/or diagnosis.

An assistant (PA, nurse, etc.) may perform a physical exam at the diagnostic center and store the data in an electronic format for the physician to review. In one example, a technician at the diagnostic center may draw blood, obtain x-rays, and the like. The physician's assistant may follow a preset protocol provided by the physician, such as obtaining certain diagnostic tests if the patient's temperature is greater than 101 degrees Fahrenheit. Additionally or alternatively, the virtual clinic may process the data from the diagnostic center and automatically suggest a diagnosis and a treatment plan which can then be reviewed by the physician and/or physician's assistant. Details of the automatic suggestion feature is found in U.S. patent application Ser. No. 09/760,917 which is hereby incorporated by reference.

A robot at the diagnostic center may be the administrator or, alternatively, work with the administrator. In some embodiments, the physician may direct the robot via the virtual clinic to perform an examination or surgery on the patient at the diagnostic center. For example, the robot (or the diagnostic center) may provide images, data, sound, or any combination thereof, to the physician through the virtual clinic. The physician may then control the robot, provide instructions, or otherwise control the procedure from a remote location.

In various embodiments, the diagnostic center includes any system with a processor and memory. Further, the diagnostic center may include a network interface, a communication interface, and diagnostic testing equipment. The network interface may be any connection to a network configured to communicate with the virtual clinic.

The communication interface may be configured to establish real-time communication between the administrator at the diagnostic center and the specialist via the virtual clinic. In one example, the communication interface includes VOIP capabilities to establish the communication. The communication interface may also include a graphical user interface (GUI) for interacting with the user and/or administrator. The communications interface may include, but is not limited to, a camera, microphone, speakers, or any combination thereof, for communicating with people via the virtual clinic.

A diagnostic center may be placed in strategic areas. For example, the diagnostic center may be remote from the user's home as well as remote from a dedicated treatment facility. A dedicated treatment facility is a hospital or similar treatment center. As discussed herein, a diagnostic center may be located at place of work where it may be cost effective for the employer rather than have loss of worker's time visiting a doctor. In another example, a diagnostic center may be used in any location where people congregate (e.g., apartment complexes, shopping centers, airports, transportation terminals, cruise liners, hotels, convention centers, stadiums, amusement parks, auditoriums, malls, sporting events, national parks, or churches).

In some embodiments, the diagnostic center is portable. In one example, the diagnostic center may be moved and used for patients during a disaster. Thus, the virtual clinic along with the portable diagnostic center can provide a substantial increase in urgently needed medical care by utilizing doctors in other areas.

For example, one or more diagnostic centers may be set up and operable after an earthquake in Northern California to attend to victims of the disaster. In this example, needed diagnostic tests are run on the victims by medical personnel and/or volunteers at the portable diagnostic centers, whereby the results are sent over one or more virtual clinic(s) to doctors not only immediately outside the affected areas of the earthquake (e.g., Sacramento), but also to doctors that are anywhere on-call (e.g., Los Angeles, San Diego, Irvine, another state, or another country). The virtual clinic(s) thereby may allow patients to receive quicker and better medical care by using doctors in remotely located areas and providing those doctors with meaningful test data to allow them to make a diagnosis and provide a course for treatment.

In some embodiments, a patient may contact their insurance carrier, whereby the insurance company puts the patient in operative communication with a physician who is known by the virtual clinic to be licensed to practice medicine in the patient's current location and to have expertise in the patient's condition.

In various embodiments, the sessions between users and specialists may be monitored through the virtual clinic. In one example, the insurance carrier or other third-party (e.g., hospital, Medicare, government) may monitor virtual clinic appointments between the patient and physician for quality control purposes. The third-party monitoring ability of the virtual clinic may be conducted randomly or be scheduled. Third-party monitoring of the virtual clinic may or may not require prior authorization of either or both of the patient and physician.

In another example, the virtual clinic may allow third-party monitoring for conferral among a plurality of specialists, peer review, and/or training purposes. In one example, the virtual clinic allows the physician to request additional expertise advice from one or more additional specialists (e.g., a consultant) or physicians remote from the patient and the requesting physician. The requesting physician can forward all information and electronic materials received by the virtual clinic and/or from the diagnostic center to the specialist, whereby the specialist can either directly communicate with the patient and/or communicate with the requesting physician. The specialist may also request additional information and/or tests.

The virtual clinic may allow one or more third-party physicians ("monitoring physicians" or supervisors) to review a consultation in real time between a patient and the physician (the "consulting physician"). In some embodiments, a monitoring physician may provide peer review comments, critiques, and/or suggestions to the consulting physician. The comments may be made textually or verbally, whereby the comments may be stored by the virtual clinic on a server and available for immediate retrieval by the consulting physician.

In some embodiments, the virtual clinic may prevent the third-party from learning the identity of the user. In one example, the virtual clinic may provide health records to the third-party and access to the communication between the user and the specialist, but bar access to any personalizing information which may reveal the identity of the user or any other sensitive information (e.g., for HIPAA purposes). In some embodiments, the virtual clinic may "anonymize" stored information (i.e., remove any or all stored personal or sensitive information) prior to allowing access to the stored information to a third-party. For example, the virtual clinic may replace any personally identifiable information (e.g., the patient's name) with generic information (e.g., "John Doe"). Similarly, the virtual clinic may eliminate or replace sensitive information, such as whether a patient has an immunological or sexually transmitted disease. The virtual clinic may also limit access to sensitive information.

In one example, the virtual clinic may authenticate a user, insurance provider, specialist, or third-party and base access rights on the authentication. As a result, the virtual machine may limit a user's (i.e., patient's) access to only their medical records and stored data associated with the user. A specialist's (i.e., physician's) access may be limited to the medical records and stored data of the specialist's patients. A third-party, however, may have greater limitations. For example, the virtual clinic may allow a trainee, supervisor, or researcher access to general information stored within the virtual clinic but not allow access to personally identifiable or sensitive information.

In various embodiments, the virtual clinic may allow the specialist access to information based on permission of the user. In one example, the user may allow the specialist access to the medical records of the user's immediate family (such as a son or daughter). As a result, the virtual clinic may provide the specialist with medical records or a link to the medical records of other individuals that the specialist might not otherwise have access to. As a result, the specialist may have greater information with which to form a diagnosis. For example, while accessing the medical records of a patient's immediate family, the physician may discover allergies or a genetically-related disease that may impact the patient's treatment, examination, and/or diagnosis. Those skilled in the art will appreciate that the virtual clinic may provide the specialist access to information over the virtual clinic in a number of different ways.

The peer review feature of the virtual clinic may allow the medical community to maintain and improve quality control on the consultations and overall patient experience as well as the integrity of the virtual clinic system. Those skilled in the art will appreciate that virtual clinic sessions with the diagnostic center may be monitored by a third-party through the diagnostic center.

The data stored by the virtual clinic, including but not limited to health records, may be analyzed by a third-party such as an insurance company. In some embodiments, the stored data is analyzed for quality assurance. In another example, the stored data is analyzed for research.

In various embodiments, the virtual clinic and/or diagnostic center may establish a real-time communication between the user and the specialist as well as a real-time communication between the specialist and the third-party (e.g., monitoring physicians, trainees, supervisors, or any combination thereof). These two communications may be combined into a three way communication such that the user, the specialist, and the third-party may communicate with each other. In other embodiments, the communication between the user and the specialist and the communication between the specialist and the third-party are separate.

The virtual clinic may allow any qualified party to review a past session with the virtual clinic or past test results. For example, the patient or physician involved in the past session may review the session or test results. In another example, one or more third-party physicians, specialists, insurance carriers, or trainees may review a past session and/or past test results.

The virtual clinic system can also be configured to facilitate follow-up appointments with the patient. The follow-up appointment can be handled by the physician, physician's assistant or a non-medical professional. Through the virtual clinic, the person conducting the follow-up appointment can review the patient's history and charts, review stored consultations, review communications with and test data from the diagnostic center, and review previous prescriptions to ensure that a thorough follow up is performed. In some examples, the follow-up may be conducted over the virtual clinic system and network using PCs or can be conducted in person at the diagnostic center.

In some embodiments, the virtual clinic system may be used to train medical students and/or doctors who are in their residency program ("trainees"). For example, the virtual clinic may be configured to allow trainees to review consultations in real time or past consultations which are stored in the system. The virtual clinic may also be configured to allow the trainee to participate in remote consultations with the patient along with an experienced physician who monitors and critiques the trainee's performance.

By participating in training through the virtual clinic, the trainee may complete some or all of the necessary training as part of completing the required residency or medical program without having to travel to a hospital. The trainees may also be required to work at a diagnostic center for a required number of hours as part of a residency or medical degree program. In some embodiments, the virtual clinic may be configured to certify or recertify experienced physicians who wish to begin or continue consulting patients through the virtual clinic system. In one example, a third-party recertification board may review stored patient consultations and associated information along with communications between the physician and the diagnostic centers as part of the recertification process.

In various embodiments, a physician may electronically prescribe medication with a pharmacy through the virtual clinic. The pharmacy may be integrated or remotely located from the diagnostic center. In some embodiments, a patient's allergies to medication may be stored by the virtual clinic. As a result, the virtual clinic may check to determine if there are any complications or possible reactions caused by the patient's allergies or possible reactions caused by one or more of the patient's other medications. Embodiments of the virtual clinic may cooperate with systems implementing embodiments described in U.S. nonprovisional patent application Ser. No. 09/760,917, entitled "Computer System for Assisting a Physician," filed Jan. 16, 2001.

In some embodiments, language translation programs (either as part of the virtual clinic or as separate software) may be used to allow patients and doctors to communicate with one another without the need of a physical translator. For example, a non-Spanish speaking physician may effectively communicate to a Spanish speaking patient by typing his course of treatment into his PC. The language translation software would then automatically translate the physician's typed communication into Spanish, whereby the translated text would then appear on the patient's PC. Additionally or alternatively, the translation software provides the patients with the translated communication audibly. The translation software program may be stored on the individual client PC terminals or on a server of the virtual clinic.

It will be appreciated by those skilled in the art, that the virtual clinic may be used for any animal, not just human health care. For example, the user may be an pet or animal owner and the specialist may be a veterinarian. Similarly, the diagnostic center may be located, for example, at an animal care facility (e.g., Humane Society).

Further, the virtual clinic is not limited to health care. In some embodiments, the virtual clinic along with the diagnostic centers may be used to allow a user to communicate with an expert (i.e., specialist) in a particular area of expertise for repairs of a product. For example, the virtual clinic system may be used in the automotive repair industry in which a user brings the user's vehicle to a diagnostic center to have the vehicle repaired. At the diagnostic center, tests may be performed and other information may be collected by a diagnostic technician (i.e., an administrator of the diagnostic center). The diagnostic technician may be certified in performing the tests, working with the virtual clinic system, and/or performing the actual repair. Once the tests are performed and/or other needed information is obtained, the results and/or other information are electronically communicated using the virtual clinic system to the certified technician (e.g., the certified mechanic) to repair the vehicle. The certified technician can review the test results and/or collected information to direct further tests or recommend a course of action. In the example, the certified technician can determine the cause of the problem from the information provided from the diagnostic center and identify, to the diagnostic technician (i.e., administrator at the diagnostic center), the part that needs to be repaired or replaced. In one embodiment, the owner can repair the car once the certified technician has diagnosed the problem.

In some embodiments, specific instructions may be provided to the diagnostic technician to aid in the repair or replacement of the part. In one example, the virtual clinic is connected to a database of all OEM and after market products (along with internal and/or external model and part numbers) which can be viewed and selected by the certified technician and/or customer. Upon the parts being selected, the virtual clinic automatically provides the list of the selected parts (along with ID, model numbers, or part numbers) to the diagnostic technician to ensure that the correct parts are installed on the vehicle. In some embodiments, the virtual clinic system is linked to a repair database, whereby the virtual clinic system automatically retrieves and displays step by step instructions on how to repair or replace the part from the repair database.

The virtual clinic can also be applied to repair or replacement of items including, but not limited to, computers and computer peripheral equipment, consumer electronics, vehicles other than automobiles (e.g., aircraft, boats, snowmobiles), medical equipment, and manufacturing/industrial as well as commercial equipment (e.g., copy machines).

In various embodiments, the functions described herein may be performed by a specialist device, a user device, and a virtual clinic device. Each of the specialist device, the user device, and the virtual clinic device may comprise any digital device with at least one processor and memory (e.g., a computer). In various embodiments, each of a medical professional device, a patient device, and a diagnostic center may also comprise any digital device with at least one processor and memory.

The user may communicate with the virtual clinic through the user device. Similarly, the specialist may communicate with the virtual clinic through the specialist device. The virtual clinic device runs the virtual clinic. the diagnostic center may also comprise a diagnostic center device which may communicate with the virtual clinic.

In various embodiments, the virtual clinic receives demographics of the user (e.g., patient) as described herein. The demographics may be used for marketing by one or more specialists (e.g., physicians), insurance companies, other vendors, or any combination thereof. In one example, an email is sent or a brochure is mailed to the user based on demographic information retained by the virtual clinic.

While embodiments has been depicted and described, such references do not imply a limitation on the invention, and no such limitation is to be inferred. The invention is capable of considerable modification, alternation, and equivalents in form and function, as will occur to those ordinarily skilled in the pertinent arts and having the benefit of this disclosure. The depicted and described embodiments of the invention are exemplary only, and are not exhaustive of the scope of the invention. Consequently, the invention is intended to be limited only by the spirit and scope of the appended claims, giving full cognizance to equivalents in all respects.

Those skilled in the art will appreciate that some or all of the features of the virtual clinic may be performed by a software program. A software program includes executable code that may be stored on a computer readable medium. The computer readable medium may comprise dynamic and/or static memory. For example, the computer readable medium may comprise RAM, ROM, flash memory, NOR memory, NAND memory, CD Rom, a hard drive, DVD, floppy, or any other kind of memory. The executable code is executable by a processor such as a processor within a computer.

What is claimed is:

1. A method comprising:
   establishing a virtual clinic on a network, the virtual clinic having working relationships with specialists;
   establishing a real-time communication between a user and a particular one of the specialists via the virtual clinic;
   providing user information to the particular one of the specialists via the virtual clinic;
   providing instructions from the particular one of the specialists to the user via the virtual clinic to perform a test using diagnostic test equipment operatively coupled to a diagnostic center at a remote location away from the user's home and away from a dedicated treatment facility, and the diagnostic center being administered by an administrator who is not a licensed physician;
   providing a test result to the particular one of the specialists via the virtual clinic; and
   receiving and storing a diagnosis from the specialist.

2. The method of claim 1, further comprising storing locations of a plurality of diagnostic centers, storing a list of diagnostic testing equipment present at each different diagnostic center, generating a list of diagnostic centers from the plurality of diagnostic centers based at least in part on proximity to the user, and providing the list of diagnostic centers to the user.

3. The method of claim 2, wherein the list of diagnostic centers is also based at least in part on the request for the particular one of the specialists.

4. The method of claim 1, further comprising establishing a real-time communication between the particular one of the specialists and a consultant via the virtual clinic during the real-time communication between the user and the particular one of the specialists.

5. The method of claim 4, wherein the consultant does not have access to an identity of the user.

6. The method of claim 1, further comprising providing access to the real-time communication between the user and the particular one of the specialists to a third-party.

7. The method of claim 6, wherein the third-party is a trainee.

8. The method of claim 6, wherein the third-party is a peer to the particular one of the specialists.

9. The method of claim 1, wherein the particular one of the specialists is a physician and the user is a patient.

10. The method of claim 1, further comprising receiving the user information and determining the particular one of the specialists based on the user information and specialist information.

11. The method of claim 1, further comprising establishing a real-time communication between the particular one of the specialists and a supervisor via the virtual clinic during the real-time communication between the user and the particular one of the specialists.

12. The method of claim 1, further comprising storing the communication between the user and the particular one of the specialists and enabling access to the stored communication to a third-party.

13. A system comprising:
   a specialist device for use by a specialist and configured to receive user information from a virtual clinic, provide instructions to a user via the virtual clinic to perform a test with diagnostic test equipment operatively coupled to a diagnostic center at a remote location away from the user's home and away from a dedicated treatment facility, receive a test result from the virtual clinic, and provide a diagnosis of the user via the virtual clinic;
   a user device for use by the user and configured to provide a request for the specialist to the virtual clinic and provide the test result to the virtual clinic using the diagnostic test equipment; and
   a virtual clinic device configured to provide specialist information to the user device and establish real-time communication between the specialist device and the user device.

14. The system of claim 13, wherein the virtual device is further configured to store locations of a plurality of diagnostic centers, to store a list of diagnostic testing equipment present at each different diagnostic center, to generate a list of diagnostic centers from the plurality of diagnostic centers based at least in part on proximity to the user, and to provide the list of diagnostic centers to the user device.

15. The system of claim 14, wherein the list of diagnostic centers is generated based at least in part on the request for the specialist.

16. The system of claim 13, wherein the virtual clinic device is further configured to establish a real-time communication between the specialist and a consultant via the virtual clinic during the real-time communication between the user and the specialist.

17. The system of claim 16, wherein the virtual device is further configured to protect the anonymity of the user from the consultant.

18. The system of claim 13, wherein the virtual clinic device is further configured to provide access to the real-time communication between the user and the specialist to a third-party.

19. The system of claim 18, wherein the third-party is a trainee.

20. The system of claim 18, wherein the third-party is a peer.

21. The system of claim 13, wherein the specialist is a physician and the user is a patient.

22. The system of claim 13, wherein the virtual clinic device is further configured to receive the user information from the user device, to determine the specialist based on the user information and the specialist information, and to provide at least some specialist information to the user device based on the determination.

23. The system of claim 13, wherein the virtual clinic device is further configured to establish a real-time communication between the specialist and a supervisor via the virtual clinic during the real-time communication between the user and the specialist.

24. The system of claim 13, wherein the virtual clinic device is further configured to store the communication between the user and the specialist and enable access to the stored communication to a third-party.

25. A method comprising:
   establishing a virtual clinic on a network, the virtual clinic having working relationships with specialists;
   establishing real-time communication between an administrator who is not a licensed physician at a diagnostic center and a particular one of the specialists via the virtual clinic, the diagnostic center being at a remote location away from a user's home and away from a dedicated treatment facility;
   receiving instructions to perform a test with diagnostic test equipment operatively coupled with the diagnostic center, the instructions received from the particular one of the specialists; and
   providing a test result from the diagnostic test equipment to the specialist via the virtual clinic.

26. The method of claim 25, wherein the diagnostic center is portable.

27. The method of claim 25, wherein the diagnostic center sells medical or medical-related products.

28. The method of claim 25, wherein the administrator is not medically trained.

29. The method of claim 25, wherein the user is an owner of a car, the particular one of the specialists is a car mechanic, and the test is performed on the user's car.

30. The method of claim 25, wherein the user is an owner of an animal, the particular one of the specialists is a veterinarian, and the test is performed on the user's animal.

31. A diagnostic center comprising:
   a communication interface configured to establish real-time communication between an administrator who is not a licensed physician at the diagnostic center and a specialist via a virtual clinic, the diagnostic center located at a remote location away from a user's home and away from a dedicated treatment facility; and
   a test interface operatively coupled to diagnostic testing equipment, the test interface configuring the diagnostic test equipment to perform a test;
   wherein the communication interface is operative to provide a test result to a specialist via the virtual clinic.

32. The diagnostic center of claim 31, wherein the diagnostic center is portable.

33. The diagnostic center of claim 31, wherein the diagnostic center sells medical or medical-related products.

34. The diagnostic center of claim 31, wherein the administrator is not medically trained.

35. The diagnostic center of claim 31, wherein the user is an owner of a car, the specialist is a car mechanic, and the test is performed on the user's car.

36. The diagnostic center of claim 31, wherein the user is an owner of an animal, the specialist is a veterinarian, and the test is performed on the user's animal.

37. A method comprising:
   using a processor to establish real-time communication between a user and a specialist via a virtual clinic;

providing user information to the specialist via the virtual clinic;

providing instructions from the specialist to the user via the virtual clinic to perform a test using diagnostic test equipment operatively coupled to a diagnostic center at a remote location away from the user's home and away from a dedicated treatment facility, and the diagnostic center being administered by an administrator who is not a licensed physician;

providing a test result to the specialist via the virtual clinic; and receiving and storing a diagnosis from the specialist.

38. A method comprising:

using a processor to establish real-time communication between an administrator who is not a licensed physician at a diagnostic center and a specialist via a virtual clinic, the diagnostic center being at a remote location away from a user's home and away from a dedicated treatment facility;

receiving instructions to perform a test with diagnostic test equipment operatively coupled with the diagnostic center, the instructions received from the specialist; and providing a test result from the diagnostic test equipment to the specialist via the virtual clinic.

* * * * *